United States Patent [19]

Wojtowicz et al.

[11] 4,220,768

[45] Sep. 2, 1980

[54] PROCESS FOR THE PRODUCTION OF POLYCHLOROISOCYANURIC ACIDS

[75] Inventors: John A. Wojtowicz, Cheshire; Michael Scardera, Hamden, both of Conn.

[73] Assignee: Olin Corporation, New Haven, Conn.

[21] Appl. No.: 906,908

[22] Filed: May 18, 1978

[51] Int. Cl.$^2$ ............................................. C07D 251/28
[52] U.S. Cl. ..................................................... 544/190
[58] Field of Search ........................................... 544/190

[56] References Cited

U.S. PATENT DOCUMENTS

| | | | |
|---|---|---|---|
| 3,453,274 | 7/1969 | Murrin et al. | 260/248 |
| 3,941,784 | 3/1976 | Nelson et al. | 260/248 |
| 4,087,608 | 5/1978 | Balabar et al. | 544/190 |

FOREIGN PATENT DOCUMENTS 1124042  9/1962  Fed. Rep. of Germany.

*Primary Examiner*—John M. Ford
*Attorney, Agent, or Firm*—James B. Haglind; Donald F. Clements

[57] ABSTRACT

A process for the production of polychloroisocyanuric acids in which a depressant is added to the reaction mixture. The polychloroisocyanuric acid particles produced have improved filterability and the formation of foam during the reaction is greatly reduced. Depressants employed are alkali metal salts of alkyl esters or sulfonated alkyl esters of dicarboxylic acids or ethylene oxide terminated alkoxylated alcohols having a cloud point of up to about 50° C.

13 Claims, No Drawings

PROCESS FOR THE PRODUCTION OF POLYCHLOROISOCYANURIC ACIDS

This invention relates to a process for the production of polychloroisocyanuric acids by the chlorination of cyanuric compounds. Polychloroisocyanurates are well-known products used in washing, bleaching and sanitizing applications.

In the commercial production of polychloroisocyanuric acids, chlorine gas is continuously introduced into a reaction mixture containing a slurry or solution of a cyanuric acid compound. The cyanuric acid compound is chlorinated to produce a polychloroisocyanuric acid such as dichloroisocyanuric acid, trichloroisocyanuric acid, or mixtures of the two, depending on the proportions of reactants employed. The polychloroisocyanuric acid in the reaction mixture as particles of a crystalline solid, is separated and dried. Where the separation is done by filtering, the crystalline particles produced by these processes retain considerable amounts of water, increasing the separation time and also the requirements for drying the product.

In addition, the continuous introduction of chlorine gas into the reaction mixture results in the undesirable formation of foam or froth.

It is an object of the present invention to provide a process for the production of polychloroisocyanuric acids having improved separation properties.

An additional object of the present invention is to provide a process for the production of polychloroisocyanuric acids in which the formation of foam is inhibited.

These and other objects of the invention are accomplished in a process for the production of a polychloroisocyanuric acid by the reaction of chlorine gas with a cyanuric compound selected from the group consisting of cyanuric acid, alkali metal cyanurates, and alkaline earth metal cyanurates, in a reaction mixture and recovering said polychloroisocyanuric acid from said reaction mixture, the improvement which comprises adding to said reaction mixture a depressant selected from the group consisting of alkali metal salts of alkyl esters or sulfonated alkyl esters of dicarboxylic acids, where the dicarboxylic acids are succinic acid or glutaric acid, and ethylene oxide terminated alkoxylated alcohols having a cloud point of up to about 50° C.

In the novel process of the present invention, the reaction mixture includes a cyanuric compound. Suitable cyanuric compounds include alkali metal cyanurates, alkaline earth cyanurates and cyanuric acid. Alkali metal cyanurates include those in which the alkali metal is sodium or potassium and where the cyanurate is monosodium or monopotassium cyanurate, disodium or dipotassium cyanurate and trisodium or tripotassium cyanurate. Alkaline earth cyanurates which may be employed include calcium cyanurate or magnesium cyanurate. Preferred embodiments of the cyanurates are alkali metal cyanurates such as sodium or potassium cyanurate. Where cyanuric acid is used as the cyanuric compound, the reaction mixture also contains an alkali metal hydroxide such as sodium hydroxide or potassium hydroxide, or an alkaline earth metal hydroxide such as calcium hydroxide or magnesium hydroxide. These are added in amounts sufficient to neutralize the hydrochloric acid produced during the reaction of the chlorine gas with the cyanuric acid.

Chlorine gas is introduced into the reaction mixture in amounts sufficient to produce a polychloroisocyanuric acid such as dichloroisocyanuric acid, trichloroisocyanuric acid or mixtures of dichloroisocyanuric acid and trichloroisocyanuric acid. The chlorine gas may be the sole chlorinating agent or it may be supplemented by the addition to the reaction mixture of other chlorinating agents such as hypochlorous acid or hypochlorites. Required amounts or ratios of chlorinating agents and the cyanuric compound to produce polychloroisocyanuric acid are known and are described, for example, in U.S. Pat. No. 3,757,018, issued Sept. 4, 1973, to R. N. Mesiah; U.S. Pat. No. 3,810,982, issued May 14, 1974, to R. N. Mesiah; U.S. Pat. No. 3,835,134, issued Sept. 10, 1974, to H. W. Schiessl, D. L. Sawhill and S. K. Bhutani; and U.S. Pat. No. 3,835,135, issued Sept. 10, 1974, to D. L. Sawhill.

In the above processes, chlorine gas is continuously introduced into the reaction mixture to chlorinate the cyanuric compound. The reaction mixture is agitated to provide improved contact between the chlorine gas and the cyanuric compound. As the reaction proceeds, foam or froth is produced in which particles of the polychloroisocyanuric acid are thought to be suspended in bubbles of chlorine gas. The small particles of polychloroisocyanuric acid produced by these processes are difficult to filter, and when dried, form a large proportion of fines in the final product.

In the improved process of the present invention, particles of polychloroisocyanuric acids are produced having improved filterability, increased particle sizes, and, in the dried product, a lower proportion of fines. This improvement is obtained by the addition of a selective group of chemical compounds as depressants.

Suitable depressants are ethylene oxide terminated alkoxylated alcohols having a cloud point of up to about 50° C. Examples of these non-ionic depressants include compounds of the following formula:

$$RO(CH_2-CH_2-O)_x-H \quad (I)$$

where R represents an aliphatic group having from about 10 to about 18 carbon atoms, and x represents a number of from about 1 to about 7. Alcohols which may be employed to provide the aliphatic group R include primary, secondary or tertiary alcohols and thus may possess a straight or branched chain of carbon atoms. Examples of suitable alcohols include ethyloctanol, decanol, isodecanol, undecanol, dodecanol, isododecanol, methyldodecanol, tridecanol, tetradecanol, pentadecanol, hexadecanol, heptadecanol and octadecanol.

Preferred alcohols are those in which the aliphatic chain has from about 12 to about 15 carbon atoms. The alcohols are exemplified by dodecanol, isododecanol, methyldodecanol, tridecanol, tetradecanol and pentadecanol.

Also suitable as depressants in the novel process of the present invention are nonionic compounds having the formula:

$$AO-(CH_2-CH-O)_y-(CH_2-CH_2-O)_x-H \quad (II)$$
$$\quad\quad\quad\quad\quad |$$
$$\quad\quad\quad\quad\quad A'$$

where A represents a substantially linear hydrocarbon, and more particularly an alkyl group, having an average of from about 6 to about 10 carbon atoms; A' represents methyl or ethyl, preferably methyl; y represents a number from 0 to about 8 and preferably from about 0 to about 4; and x represents a number of from about 1 to about 9 and preferably from about 4 to about 7; with the proviso that where A is about 10, y is greater than 0. The A group, as noted above, is substantially or predominantly linear which means there is essentially no branching.

The A group is derived from a linear alcohol and generally from a mixture of alcohols. Due to the nature of the processes by which these alcohols are prepared, there may be small amounts of branched chain alcohols present. Generally the presence of such branched chain alcohols in amounts less than about 15 percent of the total alcohol content by weight, will not adversely affect the overall properties of the final product. The terms linear or substantially linear hydrocarbon when used in the specification and claims with respect to A are intended to include such small amounts of branching as defined above. The number of carbon atoms referred to for A is an average number since commercial grade alcohols are generally a mixture of more than one alcohol. Preferably the A group will have an average of about 8 carbon atoms.

In Formulas I and II, the values of x and y are actually average numbers determined by the weight of that particular alkylene oxide substituent used.

The cloud points of these nonionic depressants are no higher than about 50° C. The cloud point may be determined by any suitable method such as American Society for Testing Materials Method D2024-65 Cloud Point for Nonionic Surfactants.

In addition, suitable as depressants in the improved process of the present invention are anionic alkali metal salts of esters of dicarboxylic acids having the formula:

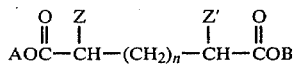

$$AOC-CH-(CH_2)_n-CH-COB$$
with O above each C=O and Z, Z' above the respective CH groups.

where A is as defined above; B represents A or an alkali metal; Z and Z' are independently selected from the group consisting of H, SO$_3$H or SO$_3$M; M represents an alkali metal; n is 0 or 1; with the proviso that where B is A, Z is SO$_3$M, and where Z and Z' are H or SO$_3$H, B is an alkali metal.

Suitable as anionic depressants of this type are alkali metal salts of monoesters of succinic acid or glutaric acid including hexyl, heptyl, octyl, nonyl and decyl esters. Also suitable are alkali metal sulfonated diesters of succinic acid or glutaric acid such as dihexyl, diheptyl, dioctyl, dinonyl, and didecyl, with dihexyl, dioctyl and didecyl being preferred. While any alkali metal may be used to form the salts, preferred alkali metals are sodium or potassium.

The depressants of this invention may be employed in any suitable amounts, such as amounts of from about 5 to about 500, and preferably from about 20 to about 150 parts per million by weight of the reaction mixture to achieve surprising results in preventing the formation of foam. In addition, the particles of polychloroisocyanuric acids produced are more readily filtered as the filter cake retains significantly less water.

While not wishing to be bound by theory, it is thought that these selected depressants, when present in the reaction mixture, effectively inhibit the chlorine gas bubbles from removing solid particles of polychloroisocyanuric acid from the aqueous media and producing undesired foam or froth. The particles thus remain in the aqueous media where they have an opportunity to form larger crystalline solids which reduces the fines content of the final product. The term "depressant" is used to define an agent which causes the lessening or depressing of the formation of foam or froth and is similar to the use of this term in processes such as ore flotation.

The improvement of the present invention is particularly applicable to processes for the production of polychloroisocyanuric acids such as those of U.S. Pat. Nos. 3,835,134 and 3,835,135 previously referred to. In these processes, an excess of chlorine gas may be used to remove from the reaction mixture any gaseous by-products such as nitrogen trichloride which may be formed during the reaction. The reaction mixture includes an aqueous slurry of a monoalkali metal cyanurate, such as monosodium cyanurate, chlorine gas, and either an alkali metal hypochlorite or hypochlorous acid. Reaction conditions for producing polychloroisocyanuric acid by these processes include temperatures in the range of from about $-5°$ to about 45° C. and a pH of from about 3 to about 4.5. The entire disclosures of U.S. Pat. No. 3,835,134 and U.S. Pat. No. 3,835,135 are incorporated by reference herein.

The depressants of the present invention may be added to the reaction mixture in any suitable manner. For example, they may be added directly or introduced into the reaction mixture in the aqueous slurry of the cyanuric compound or in a solution of hypochlorous acid or an alkali metal hypochlorite if these are employed.

The process of the present invention is further illustrated by the following examples. All percentages are by weight unless otherwise specified.

EXAMPLE 1

To an overflow reactor was added 89 g. of trichloroisocyanuric acid, 911 grams of a 7.35 percent NaCl solution and 40 ppm of an ethoxylated tridecanol of Formula I having an average of 6 moles of ethylene oxide and a cloud point of less than 0° C., as a depressant. Hypochlorous acid (7.4 percent by weight of HOCl) was produced in a separate reactor by the reaction of chlorine with NaOCl. The hypochlorous acid solution contained sufficient amounts of the same depressant to maintain a concentration of 40 ppm in the reactor. Over the reaction period of 60 minutes, 2.5 moles of the above hypochlorous acid solution were fed at a uniform rate to the overflow reactor. Simultaneously fed to the overflow reactor during the reaction period were 1.20 moles of an aqueous slurry of monosodium cyanurate and 2.4 moles of chlorine gas. The reactor was externally cooled to maintain the temperature of about 13° C. and the reaction mixture was stirred. The reactor effluent was collected in a filter vessel and filtered intermittently to produce a filter cake which was washed with water. After washing, the filter cake had a water content of 6.1 percent by weight. The product dried in a forced draft oven at 100° C. for one hour, had an available chlorine content of 91.3 percent and was obtained in a yield of 90 percent. Substantially no foaming occurred during the reaction.

EXAMPLE 2

The procedure of Example 1 was repeated with the only change being the substitution of a sodium sulfonated dialkyl succinate (Diamond Shamrock Corp.

Nopco ® 1186A) as a depressant for the ethoxylated tridecanol. The initial amount of wetting agent was 225 ppm and the hypochlorous acid contained sufficient wetting agent to maintain a concentration of 25 ppm in the reactor. After washing, the filter cake was found to have retained a water content of 12.9 percent by weight.

COMPARATIVE EXAMPLE A

The procedure of Example 1 was repeated with the only change being the omission of a depressant from the reaction mixture. After washing, the filter cake was found to have retained a water content of 22.7 percent by weight.

Examples 1 and 2, employing a novel depressant of the present invention, show surprising reductions in the retention of water in the filter cake over that obtained in the absence of a depressant in Comparative Example A. The filter cake from Comparative Example A retained a water content of 22.7 percent by weight while Examples 1 and 2 retained water contents of only 6.1 and 12.9 percent by weight respectively.

EXAMPLE 3

An aqueous slurry (1000 grams) containing 8.9 percent of trichloroisocyanuric acid and 7.4 percent of sodium chloride was added to a cylindrical glass reactor equipped with a stirrer and cooled to maintain a temperature of 15° C. Chlorine gas was continuously sparged through the slurry at the rate of 1 gram per minute. After sufficient chlorine had been added to saturate the solution, the formation of foam was observed. After allowing sufficient time for the foam height to reach an equilibrium, the foam height was measured and found to be 60 millimeters. An ethoxylated tridecanol, having an average of 6 moles of ethylene oxide and a cloud point of less than 0° C., was added to the slurry in an amount of 21 parts per million based on the weight of the reaction mixture. After the foam height had again reached an equilibrium, it was measured and found to be 15 millimeters. A period of about 5 minutes was allowed to elapse and the foam height remeasured and found to be 18 millimeters. A second increment of 22 parts per million of the ethoxylated aliphatic alcohol reduced the foam height to 8 millimeters. No change in the foam height was found after about 5 minutes. A third increment of 21 parts per million reduced the foam height to 5 millimeters. No further change in the foam height was found after 5 minutes. Further additional increments of the depressant were not required. This example shows a significant decrease in the height of foam when using an ethoxylated tridecanol having a cloud point of up to about 50° C. as a depressant in a reaction mixture simulating that which would be employed in a process for the production of trichloroisocyanuric acid.

EXAMPLE 4

The procedure of Example 3 was duplicated exactly with the exception that an alkoxylated aliphatic alcohol (Olin Corporation Poly-Tergent ® SL-42) was used as the depressant and each increment added to the reaction mixture was 25 parts per million. The nonionic ethylene oxide terminated alkoxylated aliphatic alcohol was of the type of Formula II where the aliphatic group had an average of 6 to 10 carbon atoms and had a cloud point of 42° C. The results are recorded in Table I below.

EXAMPLE 5

The procedure of Example 4 was duplicated with the exception that sodium dialkyl sulfosuccinate (Diamond Shamrock Nopco ® 1186A), an anionic depressant was substituted for Poly-Tergent ® SL-42. Results of Example 5 are recorded in Table I below.

EXAMPLE 6

The procedure of Example 4 was repeated exactly with the exception that sodium dialkyl sulfosuccinate (American Cyanamid Company Aerosol ® OT 75%), an anionic depressant was used in place of Poly-Tergent ® SL-42. Recorded in Table I below are the results of Example 6.

COMPARATIVE EXAMPLES B, C, D AND E

The procedure of Example 4 was repeated with the exception that for the alkoxylated aliphatic alcohol the following materials were substituted:

Comparative Example B—an ethoxylated nonylphenol (Olin Corp. Poly-Tergent ® B-150);

Comparative Example C—an ethylene oxide terminated alkoxylated aliphatic alcohol (Olin Corp. Poly-Tergent ® SL-62) having a cloud point of 62° C.;

Comparative Example D—a sodium alkylaryl ether sulfate (Rohm and Haas Co. Triton ® W-30); and Comparative Example E—a sulfonated amide (Stepan Chemical BioSoft ® N-21).

The results of Comparative Examples B, C, D and E are recorded in Table I below.

TABLE I

REDUCTION IN FOAM HEIGHT DURING CHLORINATION OF TRICHLOROISOCYANURIC ACID SLURRY

| Example No. | Wetting Agents | Amounts (parts per million) | | Foam Height (in millimeters) | |
|---|---|---|---|---|---|
| | | | | Start | End |
| 4 | Ethylene oxide terminated Alkoxylated aliphatic alcohol (Poly-Tergent ® SL-42) (Cloud point 42° C.) | Initial | 25 | 60 | 25 |
| | | 1st Increment | 25 | 25 | 18 |
| | | 2nd Increment | 25 | 20 | 15 |
| 5 | Sodium dialkyl sulfosuccinate (Nopco ® 1186A) | Initial | 25 | 60 | 5 |
| | | 1st Increment | 25 | 5 | 3–5 |
| | | 2nd Increment | 25 | 3–5 | 2 |
| 6 | Sodium Dialkyl sulfosuccinate (Aerosol ® OT 75%) | Initial | 25 | 60 | 20 |
| | | 1st Increment | 25 | 25 | 10 |
| | | 2nd Increment | 25 | 10 | 5–7 |
| Comparative Examples | | | | | |
| B | Ethoxylated nonylphenols (Poly-Tergent ® B-150) | Initial | 25 | 60 | 55 |
| | | 1st Increment | 25 | 55 | 45 |

TABLE I-continued

REDUCTION IN FOAM HEIGHT DURING CHLORINATION OF TRICHLOROISOCYANURIC ACID SLURRY

| Example No. | Wetting Agents | | Amounts (parts per million) | Foam Height (in millimeters) | |
|---|---|---|---|---|---|
| | | | | Start | End |
| C | Ethylene oxide terminated alkoxylated aliphatic alcohol (Poly-Tergent ® SL-62) (Cloud point 62° C.) | Initial | 25 | 60 | 50 |
| | | 1st Increment | 25 | 60 | 60 |
| | | 2nd Increment | 25 | 60 | 60 |
| D | Sodium alkylaryl ether sulfate (Triton ® W-30) | Initial | 25 | 60 | 30 |
| | | 1st Increment | 25 | 45 | 35 |
| | | 2nd Increment | 25 | 35 | 30 |
| E | Sulfonated amide (BioSoft ® N-21) | Initial | 25 | 60 | 20 |
| | | 1st Increment | 25 | 50 | 25 |

The results of Table I show that the addition of depressants in this invention significantly prevented foam formation in the slurry. Further, the foam prevention occurred during each incremental addition as evidenced by the reduction in foam height and was permanent in that the foam height did not increase greatly between incremental additions.

Comparative Examples B-E, however, show that the foam prevention was not appreciably achieved when compounds outside the scope of this invention were employed. Where reduction in foam height occurred, the reduction was only temporary.

What is claimed is:

1. In a process for the production of a polychloroisocyanuric acid by the reaction of chlorine gas with a cyanuric compound selected from the group consisting of cyanuric acid, alkali metal cyanurates and alkaline earth metal cyanurates, in a reaction mixture, and recovering said polychloroisocyanuric acid from said reaction mixture, the improvement which comprises adding to said reaction mixture a depressant selected from the group consisting of alkali metal salts of alkyl esters or sulfonated alkyl esters of dicarboxylic acids, where said dicarboxylic acids are succinic acid or glutaric acid, and ethylene oxide terminated alkoxylated alcohols having a cloud point of up to about 50° C.

2. The process of claim 1 in which said depressant is an ethylene oxide terminated alkoxylated alcohol having the formula:

$$RO(CH_2-CH_2-O)_x-H$$

where R represents an aliphatic group having from about 10 to about 18 carbon atoms, and x represents a number of from about 1 to about 7.

3. The process of claim 2 in which said R represents an aliphatic group having from about 12 to about 15 carbon atoms.

4. The process of claim 1 in which said depressant is an ethylene oxide terminated alkoxylated aliphatic alcohol having the formula:

$$AO(CH_2-\underset{A'}{CH}-O)_y-(CH_2-CH_2-O)_x-H$$

wherein A represents a substantially linear hydrocarbon having an average of from about 6 to about 10 carbon atoms; A' represents methyl or ethyl; y represents a number from 0 to about 8; and x represents a number of from about 1 to about 9.

5. The process of claim 4 in which said A' is methyl and y is from 0 to about 4.

6. The process of claim 5 in which said x is from about 1 to about 4.

7. The process of claim 1 in which said depressants are alkali metal salts of esters of dicarboxylic acids having the formula:

$$AO\overset{O}{\underset{}{C}}-\underset{\underset{}{Z}}{CH}-(CH_2)_n-\underset{\underset{}{Z'}}{CH}-\overset{O}{\underset{}{C}}OB$$

where A represents a substantially linear hydrocarbon having an average of from about 6 to about 10 carbon atoms; B represents A or an alkali metal; Z and Z' are independently selected from the group consisting of H, $SO_3H$ or $SO_3M$; M represents an alkali metal; n is 0 or 1; with the proviso that where B is A, Z is $SO_3M$, and where Z and Z' are H or $SO_3H$, B is an alkali metal.

8. The process of claim 7 in which said alkali metal is sodium or potassium.

9. The process of claim 8 in which B represents sodium.

10. The process of claim 8 in which B represents A and Z is $SO_3Na$.

11. The process of claim 10 in which said depressant is sodium dioctyl sulfosuccinate.

12. The process of claims 3, 5 or 7 in which said depressant is present in said reaction mixture in an amount from about 5 to about 500.

13. In a process for the production of a polychloroisocyanuric acid by the reaction of chlorine gas with a cyanuric compound selected from the group consisting of cyanuric acid, alkali metal cyanurates, and alkaline earth metal cyanurates, in a reaction mixture, and recovering said polychloroisocyanuric acid from said reaction mixture, the improvement which comprises adding to said reaction mixture a depressant selected from the group consisting of alkali metal salts of alkyl esters or sulfonated alkyl esters of dicarboxylic acids, where said dicarboxylic acids are succinic acid or glutaric acid.

* * * * *